US012678587B2

(12) United States Patent
Rehm

(10) Patent No.: US 12,678,587 B2
(45) Date of Patent: *Jul. 14, 2026

(54) ASSISTED FLUID DRAINAGE SYSTEM

(71) Applicant: C. R. Bard, Inc., Franklin Lakes, NJ (US)

(72) Inventor: Eric A. Rehm, Lawrenceville, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/899,727

(22) Filed: Sep. 27, 2024

(65) Prior Publication Data

US 2025/0018147 A1 Jan. 16, 2025

Related U.S. Application Data

(63) Continuation of application No. 17/373,568, filed on Jul. 12, 2021, now Pat. No. 12,121,669.
(Continued)

(51) Int. Cl.
*A61M 25/00* (2006.01)

(52) U.S. Cl.
CPC ......... *A61M 25/00* (2013.01); *A61M 25/0017* (2013.01); *A61M 2025/0019* (2013.01)

(58) Field of Classification Search
CPC .............. A61M 25/00; A61M 25/0017; A61M 2025/0019; A61M 39/10; A61M 60/211; A61M 1/804
(Continued)

(56) References Cited

U.S. PATENT DOCUMENTS

| | | | |
|---|---|---|---|
| 3,114,916 A | 12/1963 | Hadley | |
| 3,583,401 A | 6/1971 | Vailiancourt et al. | |

(Continued)

FOREIGN PATENT DOCUMENTS

| | | |
|---|---|---|
| CN | 106955208 A | 7/2017 |
| CN | 116650740 A | 8/2023 |

(Continued)

OTHER PUBLICATIONS

U.S. Appl. No. 17/701,395, filed Mar. 22, 2022 Non-Final Office Action dated Jun. 3, 2025.
(Continued)

*Primary Examiner* — Craig M Schneider
*Assistant Examiner* — Christopher M Afful
(74) *Attorney, Agent, or Firm* — Rutan & Tucker LLP

(57) ABSTRACT

Systems and methods directed to an assisted fluid drainage system including a proximal ejector pump and a distal ejector pump coupled to a drainage tube. At least one of the proximal ejector pump and the distal ejector pump can utilize a venturi effect to move a bodily fluid through the drainage tube to prevent the formation of dependent loops, which can form within fluid drainage tubes when slack portions create a positive incline. At least one of the proximal ejector pump and the distal ejector pump can include a converging section, a diffuser section, and a diverging section. A diameter of the diffuser section can be less than a diameter of the converging section or the diverging section. A controller can be coupled to the proximal ejector pump and the distal ejector pump to initiate operation of one or both of the pumps in response to an event.

15 Claims, 6 Drawing Sheets

Related U.S. Application Data

(60) Provisional application No. 63/065,917, filed on Aug. 14, 2020.

(58) Field of Classification Search
     USPC ........................................................ 141/1, 4
     See application file for complete search history.

(56)                    References Cited

U.S. PATENT DOCUMENTS

| | | | |
|---|---|---|---|
| 3,598,124 | A | 8/1971 | Andersen et al. |
| 3,661,143 | A | 5/1972 | Henkin |
| 3,861,394 | A | 1/1975 | Villari |
| 3,901,235 | A | 8/1975 | Patel et al. |
| 3,955,574 | A | 5/1976 | Rubinstein |
| 4,084,593 | A | 4/1978 | Jarund |
| 4,250,872 | A | 2/1981 | Tamari |
| 4,265,243 | A | 5/1981 | Taylor |
| 4,305,403 | A | 12/1981 | Dunn |
| 4,315,506 | A | 2/1982 | Kayser et al. |
| 4,360,933 | A | 11/1982 | Kimura et al. |
| 4,465,485 | A | 8/1984 | Kashmer et al. |
| 4,490,144 | A | 12/1984 | Steigerwald |
| 4,531,939 | A | 7/1985 | Izumi |
| 4,556,997 | A | 12/1985 | Takamiya et al. |
| 4,631,061 | A | 12/1986 | Martin |
| 4,654,029 | A | 3/1987 | D'Antonio |
| 4,747,166 | A | 5/1988 | Kuntz |
| 4,810,242 | A | 3/1989 | Sundblom et al. |
| 4,819,684 | A | 4/1989 | Zaugg et al. |
| 4,872,579 | A | 10/1989 | Palmer |
| 4,880,411 | A | 11/1989 | Fangrow, Jr. et al. |
| 4,990,137 | A | 2/1991 | Graham |
| 5,002,528 | A | 3/1991 | Palestrant |
| 5,071,411 | A | 12/1991 | Hillstead |
| 5,186,431 | A | 2/1993 | Tamari |
| 5,242,404 | A | 9/1993 | Conley et al. |
| 5,318,550 | A | 6/1994 | Cermak et al. |
| 5,359,233 | A | 10/1994 | Mumper et al. |
| 5,405,319 | A | 4/1995 | Abell et al. |
| RE35,707 | E | 12/1997 | Takamiya et al. |
| 5,738,656 | A | 4/1998 | Wagner |
| 5,813,842 | A | 9/1998 | Tamari |
| 5,894,608 | A | 4/1999 | Birbara |
| 6,007,521 | A | 12/1999 | Bidwell et al. |
| 6,106,506 | A | 8/2000 | Abell et al. |
| 6,183,454 | B1 | 2/2001 | Levine et al. |
| 7,833,186 | B1 | 11/2010 | Batiste |
| 8,266,741 | B2 | 9/2012 | Penninger et al. |
| 8,337,475 | B2 | 12/2012 | Christensen et al. |
| 8,366,692 | B2 | 2/2013 | Weston et al. |
| 8,475,419 | B2 | 7/2013 | Eckermann |
| 8,512,301 | B2 | 8/2013 | Ma |
| 9,814,866 | B1 | 11/2017 | Goswami |
| 10,391,275 | B2 | 8/2019 | Burnett et al. |
| 10,426,919 | B2 | 10/2019 | Erbey, II et al. |
| 10,506,965 | B2 | 12/2019 | Cooper et al. |
| 10,737,057 | B1 | 8/2020 | Mikhail et al. |
| 10,772,998 | B2 | 9/2020 | Luxon et al. |
| 2002/0000253 | A1 | 1/2002 | Fillmore et al. |
| 2002/0087131 | A1 | 7/2002 | Wolff et al. |
| 2002/0161317 | A1 | 10/2002 | Risk et al. |
| 2003/0078638 | A1 | 4/2003 | Voorhees et al. |
| 2004/0176746 | A1 | 9/2004 | Forral |
| 2004/0230181 | A1 | 11/2004 | Cawood |
| 2004/0236292 | A1 | 11/2004 | Tazoe et al. |
| 2004/0254547 | A1 | 12/2004 | Okabe et al. |
| 2005/0197647 | A1 | 9/2005 | Dolliver et al. |
| 2005/0209585 | A1 | 9/2005 | Nord et al. |
| 2005/0245898 | A1 | 11/2005 | Wright et al. |
| 2005/0256460 | A1 | 11/2005 | Rome et al. |
| 2005/0261619 | A1 | 11/2005 | Gay |
| 2006/0015190 | A1 | 1/2006 | Robertson |
| 2006/0079854 | A1 | 4/2006 | Kay et al. |
| 2006/0155260 | A1 | 7/2006 | Blott et al. |
| 2006/0235353 | A1 | 10/2006 | Gelfand et al. |
| 2006/0270971 | A1 | 11/2006 | Gelfand et al. |
| 2006/0271019 | A1 | 11/2006 | Stoller et al. |
| 2007/0005002 | A1 | 1/2007 | Millman et al. |
| 2007/0078444 | A1 | 4/2007 | Larsson |
| 2007/0142729 | A1 | 6/2007 | Pfeiffer et al. |
| 2007/0272311 | A1 | 11/2007 | Trocki et al. |
| 2008/0051708 | A1 | 2/2008 | Kumar et al. |
| 2008/0156092 | A1 | 7/2008 | Boiarski |
| 2008/0281254 | A1 | 11/2008 | Humayun et al. |
| 2009/0157016 | A1 | 6/2009 | Adahan |
| 2009/0157040 | A1 | 6/2009 | Jacobson et al. |
| 2009/0326483 | A1 | 12/2009 | Green |
| 2010/0042059 | A1 | 2/2010 | Pratt et al. |
| 2010/0106116 | A1 | 4/2010 | Simmons et al. |
| 2010/0130949 | A1 | 5/2010 | Garcia |
| 2010/0280435 | A1 | 11/2010 | Raney et al. |
| 2011/0060300 | A1 | 3/2011 | Weig et al. |
| 2012/0036638 | A1 | 2/2012 | Penninger et al. |
| 2012/0323144 | A1 | 12/2012 | Coston et al. |
| 2013/0218106 | A1 | 8/2013 | Coston et al. |
| 2014/0053841 | A1 | 2/2014 | Ratner |
| 2014/0200558 | A1 | 7/2014 | McDaniel |
| 2014/0200588 | A1 | 7/2014 | Anderson et al. |
| 2014/0276497 | A1 | 9/2014 | Robinson et al. |
| 2015/0126975 | A1 | 5/2015 | Wuthier |
| 2015/0290448 | A1 | 10/2015 | Pavlik |
| 2016/0135982 | A1 | 5/2016 | Garcia |
| 2016/0183819 | A1 | 6/2016 | Burnett et al. |
| 2016/0310711 | A1 | 10/2016 | Luxon et al. |
| 2017/0014617 | A1 | 1/2017 | Huici |
| 2017/0072125 | A1 | 3/2017 | Wallenås et al. |
| 2017/0136209 | A1 | 5/2017 | Burnett et al. |
| 2017/0143566 | A1 | 5/2017 | Elku et al. |
| 2017/0209630 | A1 | 7/2017 | Klusmann et al. |
| 2017/0241978 | A1 | 8/2017 | Duval |
| 2017/0312114 | A1 | 11/2017 | Glithero |
| 2018/0015251 | A1 | 1/2018 | Lampotang et al. |
| 2018/0071441 | A1 | 3/2018 | Croteau et al. |
| 2018/0104391 | A1 | 4/2018 | Luxon et al. |
| 2018/0110456 | A1 | 4/2018 | Cooper et al. |
| 2018/0125697 | A1 | 5/2018 | Ferrera |
| 2018/0177458 | A1 | 6/2018 | Burnett et al. |
| 2018/0235523 | A1 | 8/2018 | Sauder |
| 2018/0245699 | A1 | 8/2018 | Lee |
| 2018/0360424 | A1* | 12/2018 | Yurek ...................... A61B 8/12 |
| 2019/0009021 | A1 | 1/2019 | Nelson et al. |
| 2019/0009023 | A1 | 1/2019 | Diperna et al. |
| 2019/0030264 | A1 | 1/2019 | Herskovic et al. |
| 2019/0038451 | A1 | 2/2019 | Harvie |
| 2019/0046102 | A1 | 2/2019 | Kushnir et al. |
| 2019/0126006 | A1 | 5/2019 | Rehm et al. |
| 2019/0143008 | A1 | 5/2019 | Brundage et al. |
| 2019/0143094 | A1 | 5/2019 | DeMeritt |
| 2019/0151610 | A1 | 5/2019 | Fletter |
| 2019/0255242 | A1 | 8/2019 | Cull |
| 2019/0343445 | A1 | 11/2019 | Burnett et al. |
| 2020/0000979 | A1 | 1/2020 | Myers |
| 2020/0061281 | A1 | 2/2020 | Desouza et al. |
| 2020/0155751 | A1 | 5/2020 | Batiste |
| 2020/0315837 | A1 | 10/2020 | Radl et al. |
| 2021/0077007 | A1 | 3/2021 | Jouret et al. |
| 2022/0152345 | A1 | 5/2022 | Simiele et al. |
| 2022/0160949 | A1* | 5/2022 | Simiele .................. A61M 1/64 |
| 2022/0176031 | A1 | 6/2022 | Cheng et al. |
| 2022/0193366 | A1 | 6/2022 | Cheng et al. |
| 2022/0218890 | A1 | 7/2022 | Chavan |
| 2022/0218973 | A1 | 7/2022 | Chavan et al. |
| 2022/0218974 | A1 | 7/2022 | Chavan et al. |
| 2022/0273213 | A1 | 9/2022 | Sokolov et al. |
| 2022/0287689 | A1 | 9/2022 | Johannes |
| 2022/0305189 | A1 | 9/2022 | Chavan et al. |
| 2022/0330867 | A1 | 10/2022 | Conley et al. |
| 2022/0362080 | A1 | 11/2022 | McCorquodale et al. |
| 2022/0409421 | A1 | 12/2022 | Hughett et al. |
| 2023/0013353 | A1 | 1/2023 | Chavan et al. |
| 2023/0030637 | A1 | 2/2023 | Gloeckner et al. |
| 2023/0054937 | A1 | 2/2023 | Chancy et al. |
| 2023/0083906 | A1 | 3/2023 | Jones et al. |
| 2023/0277199 | A1 | 9/2023 | Duffy |

(56) References Cited

U.S. PATENT DOCUMENTS

| | | |
|---|---|---|
| 2023/0310837 A1 | 10/2023 | Gamsizlar et al. |
| 2024/0033404 A1 | 2/2024 | Ishikawa |
| 2024/0238500 A1 | 7/2024 | Simiele et al. |
| 2024/0307604 A1 | 9/2024 | Chavan |
| 2025/0009578 A1 | 1/2025 | Chancy et al. |
| 2025/0018149 A1 | 1/2025 | Cheng et al. |
| 2025/0025617 A1 | 1/2025 | Chavan et al. |
| 2025/0025620 A1 | 1/2025 | Cheng et al. |
| 2025/0040848 A1 | 2/2025 | Lai et al. |
| 2025/0177632 A1 | 6/2025 | Jones et al. |
| 2025/0186735 A1 | 6/2025 | Rehm et al. |
| 2026/0014310 A1 | 1/2026 | Chavan |

FOREIGN PATENT DOCUMENTS

| | | |
|---|---|---|
| EP | 1872752 A1 | 1/2008 |
| EP | 2417955 A2 | 2/2012 |
| EP | 2730299 A1 | 5/2014 |
| GB | 223526 | 2/1991 |
| WO | 2009026237 A1 | 2/2009 |
| WO | 2012016179 A1 | 2/2012 |
| WO | 2015019056 A1 | 2/2015 |
| WO | 2015105916 A1 | 7/2015 |
| WO | 2016012494 A1 | 1/2016 |
| WO | 2017177068 A1 | 10/2017 |
| WO | 2018136306 A1 | 7/2018 |
| WO | 2018191193 A1 | 10/2018 |
| WO | 2019004854 A1 | 1/2019 |
| WO | 2019083104 A1 | 5/2019 |
| WO | 2020033752 A1 | 2/2020 |
| WO | 2021154427 A1 | 8/2021 |
| WO | 2022159333 A1 | 7/2022 |
| WO | 2022251425 A1 | 12/2022 |
| WO | 2023086394 A1 | 5/2023 |

OTHER PUBLICATIONS

U.S. Appl. No. 17/863,898, filed Jul. 13, 2022 Final Office Action dated Jun. 3, 2025.
U.S. Appl. No. 18/274,157, filed Jul. 25, 2023 Advisory Action dated Jul. 16, 2025.
U.S. Appl. No. 18/274,157, filed Jul. 25, 2023 Final Office Action dated May 5, 2025.
U.S. Appl. No. 18/674,694, filed May 24, 2024 Notice of Allowance dated Jun. 23, 2025.
PCT/US2020/066707 filed Dec. 22, 2020 International Search Report and Written Opinion dated Apr. 15, 2021.
PCT/US2022/012373 filed Jan. 13, 2022 International Search Report and Written Opinion dated Apr. 19, 2022.
PCT/US2022/049418 filed Nov. 9, 2022 International Search Report and Written Opinion dated Feb. 10, 2023.
U.S. Appl. No. 17/373,568, filed Jul. 12, 2021 Non-Final Office Action dated Nov. 9, 2023.
U.S. Appl. No. 17/373,568, filed Jul. 12, 2021 Notice of Allowance dated Apr. 26, 2024.
U.S. Appl. No. 17/526,994, filed Nov. 15, 2021 Advisory Action dated Jan. 19, 2024.
U.S. Appl. No. 17/526,994, filed Nov. 15, 2021 Final Office Action dated Oct. 24, 2023.
U.S. Appl. No. 17/526,994, filed Nov. 15, 2021 Non-Final Office Action dated Apr. 22, 2024.
U.S. Appl. No. 17/526,994, filed Nov. 15, 2021 Non-Final Office Action dated May 10, 2023.
U.S. Appl. No. 17/526,994, filed Nov. 15, 2021 Restriction Requirement dated Jan. 3, 2023.
U.S. Appl. No. 17/532,454, filed Nov. 22, 2021 Final Office Action dated Sep. 27, 2023.
U.S. Appl. No. 17/532,454, filed Nov. 22, 2021 Non-Final Office Action dated Mar. 22, 2023.
U.S. Appl. No. 17/532,454, filed Nov. 22, 2021 Notice of Allowance dated Dec. 8, 2023.
U.S. Appl. No. 17/542,060, filed Dec. 3, 2021 Non-Final Office Action dated Jun. 27, 2023.
U.S. Appl. No. 17/542,060, filed Dec. 3, 2021 Non-Final Office Action dated Nov. 28, 2023.
U.S. Appl. No. 17/542,060, filed Dec. 3, 2021 Notice of Allowance dated Jun. 3, 2024.
U.S. Appl. No. 17/556,942, filed Dec. 20, 2021 Advisory Action dated Sep. 1, 2023.
U.S. Appl. No. 17/556,942, filed Dec. 20, 2021 Final Office Action dated Apr. 4, 2024.
U.S. Appl. No. 17/556,942, filed Dec. 20, 2021 Final Office Action dated Jul. 12, 2023.
U.S. Appl. No. 17/556,942, filed Dec. 20, 2021 Non-Final Office Action dated Jan. 31, 2023.
U.S. Appl. No. 17/556,942, filed Dec. 20, 2021 Non-Final Office Action dated Nov. 3, 2023.
U.S. Appl. No. 17/556,942, filed Dec. 20, 2021 Notice of Allowance dated Jun. 26, 2024.
U.S. Appl. No. 17/561,458, filed Dec. 23, 2021 Final Office Action dated Sep. 12, 2023.
U.S. Appl. No. 17/561,458, filed Dec. 23, 2021 Non-Final Office Action dated Jun. 16, 2023.
U.S. Appl. No. 17/561,458, filed Dec. 23, 2021 Notice of Allowance dated Dec. 6, 2023.
U.S. Appl. No. 17/561,504, filed Dec. 23, 2021 Final Office Action dated Jul. 19, 2023.
U.S. Appl. No. 17/561,504, filed Dec. 23, 2021 Non-Final Office Action dated Mar. 14, 2023.
U.S. Appl. No. 17/561,504, filed Dec. 23, 2021 Non-Final Office Action dated Nov. 27, 2023.
U.S. Appl. No. 17/561,504, filed Dec. 23, 2021 Notice of Allowance dated Jan. 22, 2024.
U.S. Appl. No. 17/571,254, filed Jan. 7, 2022 Restriction Requirement dated Oct. 4, 2024.
U.S. Appl. No. 17/796,604, filed Jul. 29, 2022 Notice of Allowance dated May 1, 2024.
U.S. Appl. No. 17/863,898, filed Jul. 13, 2022 Advisory Action dated Jan. 30, 2024.
U.S. Appl. No. 17/863,898, filed Jul. 13, 2022 Final Office Action dated Aug. 22, 2024.
U.S. Appl. No. 17/863,898, filed Jul. 13, 2022 Final Office Action dated Nov. 22, 2023.
U.S. Appl. No. 17/863,898, filed Jul. 13, 2022 Non-Final Office Action dated Jul. 17, 2023.
U.S. Appl. No. 17/863,898, filed Jul. 13, 2022 Non-Final Office Action dated Mar. 11, 2024.
U.S. Appl. No. 17/902,705, filed Sep. 2, 2022 Advisory Action dated Aug. 1, 2024.
U.S. Appl. No. 17/902,705, filed Sep. 2, 2022 Advisory Action dated Oct. 19, 2023.
U.S. Appl. No. 17/902,705, filed Sep. 2, 2022 Final Office Action dated Aug. 17, 2023.
U.S. Appl. No. 17/902,705, filed Sep. 2, 2022 Final Office Action dated May 22, 2024.
U.S. Appl. No. 17/902,705, filed Sep. 2, 2022 Non-Final Office Action dated Dec. 7, 2023.
U.S. Appl. No. 17/902,705, filed Sep. 2, 2022 Non-Final Office Action dated May 24, 2023.
U.S. Appl. No. 17/902,705, filed Sep. 2, 2022 Notice of Allowance dated Sep. 18, 2024.
U.S. Appl. No. 17/526,994, filed Nov. 15, 2021 Final Office Action dated Nov. 19, 2024.
U.S. Appl. No. 17/526,994, filed Nov. 15, 2021 Notice of Allowance dated Feb. 5, 2025.
U.S. Appl. No. 17/571,254, filed Jan. 7, 2022 Non-Final Office Action dated Feb. 13, 2025.
U.S. Appl. No. 17/863,898, filed Jul. 13, 2022 Advisory Action dated Oct. 28, 2024.
U.S. Appl. No. 17/863,898, filed Jul. 13, 2022 Non-Final Office Action dated Dec. 2, 2024.
U.S. Appl. No. 18/274,157, filed Jul. 25, 2023 Non-Final Office Action dated Jan. 17, 2025.

(56) References Cited

OTHER PUBLICATIONS

U.S. Appl. No. 18/674,694, filed May 24, 2024 Non-Final Office Action dated Mar. 3, 2025.

U.S. Appl. No. 17/751,254 filed Jan. 7, 2022 Non-Final Office Action dated Mar. 25, 2026.

U.S. Appl. No. 17/701,395 filed Mar. 22, 2022 Advisory Action dated Feb. 19, 2026.

U.S. Appl. No. 17/873,923 filed Jul. 26, 2022 Non-Final Office Action dated Jan. 27, 2026.

U.S. Appl. No. 18/274,157 filed Jul. 25, 2023 Final Office Action dated Jan. 6, 2026.

U.S. Appl. No. 18/706,737 filed May 1, 2024 Non-Final Office Action dated Mar. 13, 2026.

U.S. Appl. No. 18/882,228 filed Sep. 11, 2024 Notice of Allowance dated Feb. 5, 2026.

* cited by examiner

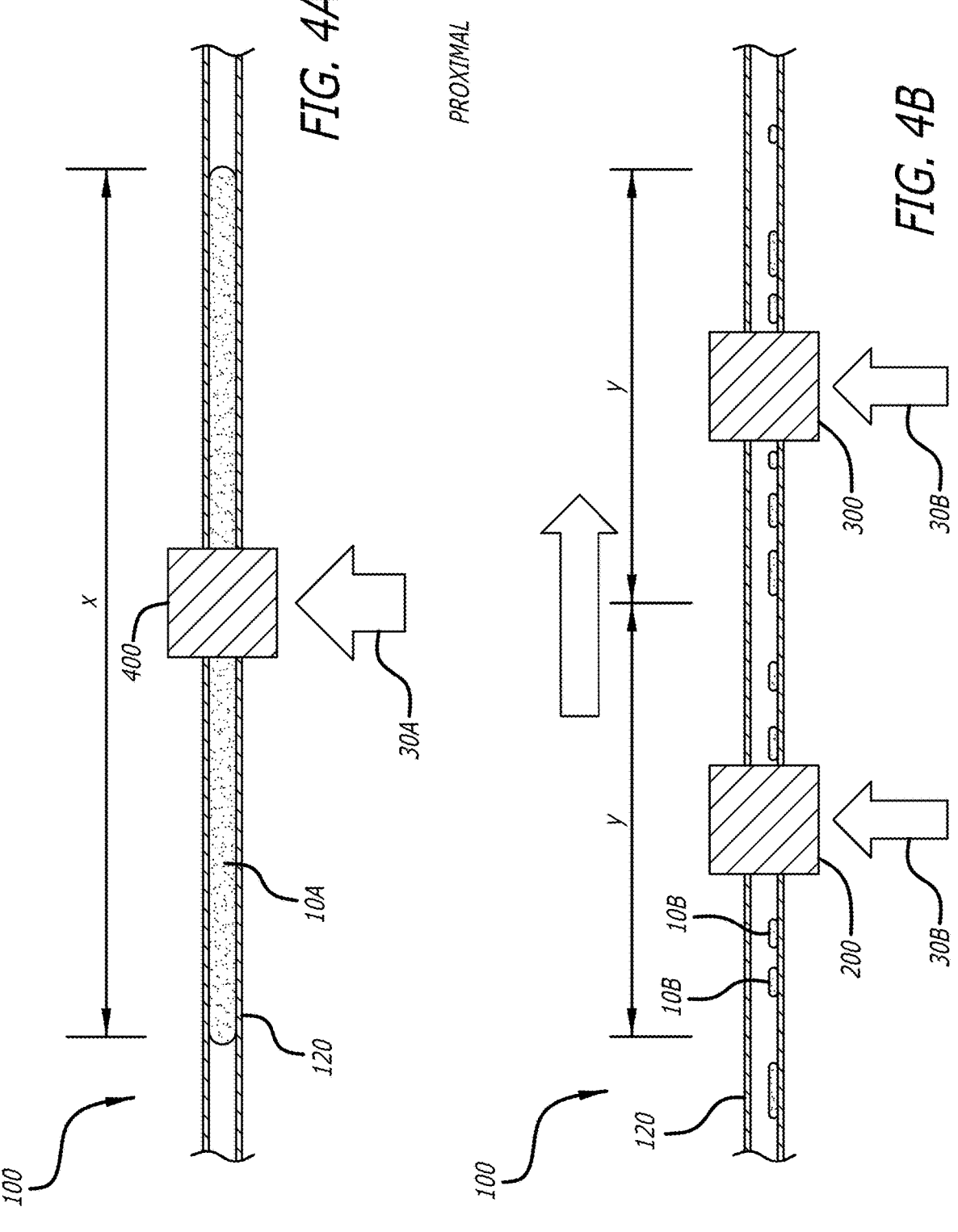

ASSISTED FLUID DRAINAGE SYSTEM

PRIORITY

This application is a continuation of U.S. patent application Ser. No. 17/373,568, filed Jul. 12, 2021, now U.S. Pat. No. 12,121,669, which claims the benefit of priority to U.S. Provisional Application No. 63/065,917, filed Aug. 14, 2020, each of which is incorporated by reference in its entirety into this application.

SUMMARY

Briefly summarized, systems and methods disclosed herein are directed to an assisted fluid drainage system including one or more vacuum pumps, e.g. ejector pump, disposed in-line with the drainage tube. The one or more vacuum pumps can use a venturi effect vacuum pump to draw a fluid in and urge the fluid through the drainage tube to prevent the formation of dependent loops. Dependent loops can form within fluid drainage tubes when slack portions of tube create a positive incline. These dependent loops trap fluid and can create a retrograde flow, leading to various complications. For example, urine pooling within a drainage tube can become a source of catheter associated urinary tract infection ("CAUTI") causing agents such as bacteria, microbes, and the like. Hospital Acquired Infections ("HAI"), such as CAUTI, are detrimental to the patient, and also incur extra costs in treating these additional complications.

Disclosed herein is a fluid drainage system including, a drainage tube defining a lumen, configured to provide fluid communication between a catheter and a collection container, and including, a distal ejector pump disposed in-line with the lumen proximate the catheter, and a proximal ejector pump disposed in-line with the lumen proximate the collection container, wherein the distal ejector pump or the proximal ejector pump is configured to urge a fluid through drainage tube while the drainage tube remains in fluid communication with the catheter.

In some embodiments, the distal ejector pump or the proximal ejector pump includes a ring drive nozzle extending annularly about the lumen. The distal ejector pump or the proximal ejector pump includes an array of drive nozzles arranged in a ring-shaped formation extending annularly about the lumen. The distal ejector pump or the proximal ejector pump includes a converging section, a diffuser section, and a diverging section. A diameter of the diffuser section is less than a diameter of one of the converging section or the diverging section. The diverging section includes a stepped expansion portion. A drive nozzle provides a drive fluid at the stepped expansion portion. The distal ejector pump or the proximal ejector pump provides a vacuum influencing a portion of the lumen that is less than an entire length of the drainage tube. The distal ejector pump influences a fluid disposed in a first portion of the lumen and the proximal ejector pump influences a fluid disposed in a second portion of the lumen, different from the first portion of the lumen.

Also disclosed is a method of draining a fluid from a catheter to a collection container including, providing a drainage tube defining a lumen, providing fluid communication between the catheter and the collection container, and including a first ejector pump disposed proximate the catheter, and a second ejector pump disposed proximate the collection container, providing a drive fluid to one of the first ejector pump or the second ejector pump, entraining a drainage fluid disposed in a distal portion of the lumen, with the first ejector pump, to urge the drainage fluid from the distal portion to a proximal portion of the lumen, and entraining the drainage fluid disposed in the proximal portion of the lumen, with the second ejector pump, to urge the drainage fluid from the proximal portion to the collection container.

In some embodiments, the drainage tube remains in fluid communication with the catheter while one of the first ejector pump or the second ejector pump entrains the drainage fluid. The first ejector pump or the second ejector pump operates continually. The first ejector pump or the second ejector pump operates intermittently. The first ejector pump and the second ejector pump operates either simultaneously or sequentially. The drainage tube includes a sample port or an inlet vent disposed distally of the first ejector pump, the vent configured to allow a gas to enter the lumen. In some embodiments, the method further includes an outlet vent disposed proximally of the proximal pump configured to allow a gas to escape. The first ejector pump or the second ejector pump includes a ring drive nozzle extending annularly about the lumen. The first ejector pump or the second ejector pump includes a converging section, a diffuser section, and a diverging section. The diverging section includes a stepped expansion portion. A drive nozzle provides a drive fluid at the stepped expansion portion.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 4A illustrates a columnized fluid disposed within a drainage tube, in accordance with embodiments disclosed herein.

FIG. 4B illustrates a mixed fluid disposed within a drainage tube, in accordance with embodiments disclosed herein.

DESCRIPTION

Figure 1:
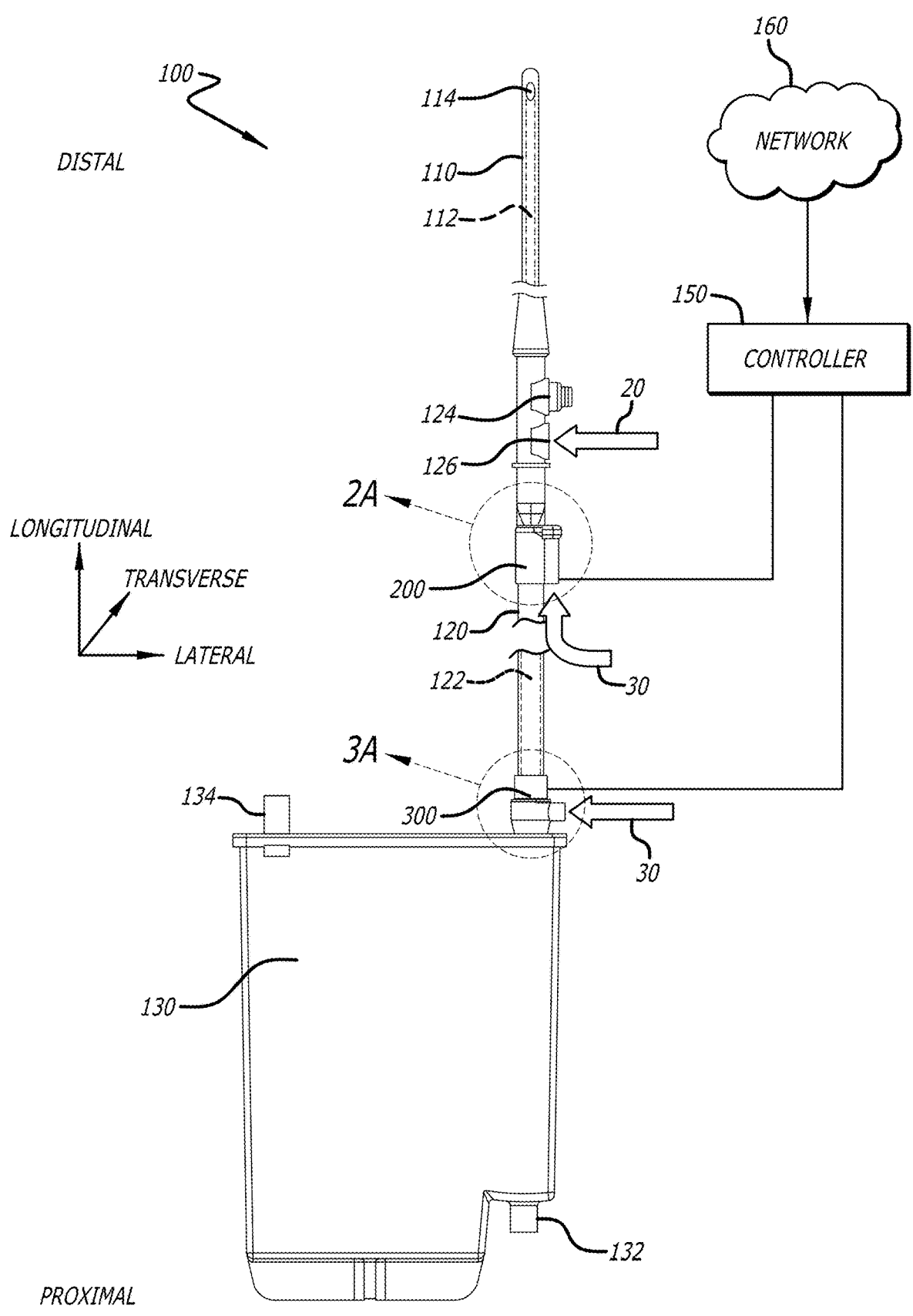
FIG. 1 illustrates an exemplary fluid drainage system including a distal pump and a proximal pump, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

In the following description, certain terminology is used to describe aspects of the invention. For example, in certain situations, the term "logic" is representative of hardware, firmware or software that is configured to perform one or more functions. As hardware, logic may include circuitry having data processing or storage functionality. Examples of such circuitry may include, but are not limited or restricted to a hardware processor (e.g., microprocessor with one or more processor cores, a digital signal processor, a programmable gate array, a microcontroller, an application specific integrated circuit "ASIC," etc.), a semiconductor memory, or combinatorial elements.

Alternatively, logic may be software, such as executable code in the form of an executable application, an Application Programming Interface (API), a subroutine, a function, a procedure, an applet, a servlet, a routine, source code, object code, a shared library/dynamic load library, or one or more instructions. The software may be stored in any type of a suitable non-transitory storage medium, or transitory storage medium (e.g., electrical, optical, acoustical or other form of propagated signals such as carrier waves, infrared signals, or digital signals). Examples of non-transitory storage medium may include, but are not limited or restricted to a programmable circuit; semiconductor memory; non-persistent storage such as volatile memory (e.g., any type of random access memory "RAM"); or persistent storage such as non-volatile memory (e.g., read-only memory "ROM," power-backed RAM, flash memory, phase-change memory, etc.), a solid-state drive, hard disk drive, an optical disc drive, or a portable memory device. As firmware, the executable code may be stored in persistent storage.

The term "computing device" should be construed as electronics with the data processing capability and/or a capability of connecting to any type of network, such as a public network (e.g., Internet), a private network (e.g., a wireless data telecommunication network, a local area network "LAN", etc.), or a combination of networks. Examples of a computing device may include, but are not limited or restricted to, the following: a server, an endpoint device (e.g., a laptop, a smartphone, a tablet, a "wearable" device such as a smart watch, augmented or virtual reality viewer, or the like, a desktop computer, a netbook, a medical device, or any general-purpose or special-purpose, user-controlled electronic device), a mainframe, internet server, a router; or the like.

A "message" generally refers to information transmitted in one or more electrical signals that collectively represent electrically stored data in a prescribed format. Each message may be in the form of one or more packets, frames, HTTP-based transmissions, or any other series of bits having the prescribed format.

The term "computerized" generally represents that any corresponding operations are conducted by hardware in combination with software and/or firmware.

As shown in FIG. 1, and to assist in the description of embodiments described herein, a longitudinal axis extends substantially parallel to an axial length of a catheter/drainage tube. A lateral axis extends normal to the longitudinal axis, and a transverse axis extends normal to both the longitudinal and lateral axes.

Unless defined otherwise, all technical and scientific terms used herein have the same meaning as commonly understood by those of ordinary skill in the art.

FIG. 1 shows an exemplary assisted fluid collection system ("system") 100, which generally includes a catheter 110, a drainage tube ("tube") 120, and a collection container ("container") 130. Exemplary catheters 110 include indwelling catheters, Foley catheters, balloon catheters, peritoneal drainage catheters, or the like, and are configured to be inserted into an orifice within the body of a patient to drain a fluid therefrom. Exemplary body fluids can include urine, blood, interstitial fluid, peritoneal fluid, saliva, mucus, or the like. In an embodiment, the catheter 110 can be inserted through the urethra and into a bladder of a patient. The catheter 110 includes an eyelet 114 that provides fluid communication with a lumen of the catheter 110, and is configured to drain a fluid, e.g. urine.

The drainage tube 120 extends from a proximal end of the catheter 110 to a collection container 130. The drainage tube 120 defines a drainage lumen 122 that provides fluid communication between the catheter lumen 112 and the collection container 130.

The drainage tube 120 can be formed of rubber, plastic, polymer, silicone, or similar suitable material. The collection container 130 can include a rigid container, a flexible collection bag, or similar suitable container for receiving a fluid, e.g. urine, drained from the catheter 110. In an embodiment, the container 130 includes a drainage outlet 132 to allow the fluid to be emptied from the collection container 130. In an embodiment, the container 130 includes an outlet vent 134 configured to allow air or similar gas to be released from the collection container 130. In an embodiment, the outlet vent 134 can include a filter, valve, or similar structure configured to allow gas to escape from the container but to prevent a liquid from passing through the outlet vent 134.

In an embodiment, the drainage tube 120 can include one or more vacuum pumps, such as a first, distal vacuum pump ("distal pump") 200 disposed in-line with the lumen of the drainage tube 120 proximate a distal end of the tube 120, and a second, proximal vacuum pump ("proximal pump") 300 disposed in-line with the lumen 122 of the drainage tube 120 proximate a proximal end of the tube 120. It will be appreciated that additional vacuum pumps disposed therebetween are also contemplated to fall within the scope of the present invention. In an embodiment, the one or more vacuum pumps, e.g. pumps 200, 300, can be identical. In an embodiment, the one or more vacuum pumps, e.g. pumps 200, 300, can differ in size, configuration, vacuum pump characteristics, flow resistance characteristics, combinations thereof, or the like.

The drainage tube 120 can further include a sample port 124 or an inlet air vent 126. The sample port 124 can include a cap, valve or similar structure configured to allow selective access to the drainage tube lumen 122 to sample a fluid disposed therein. The inlet vent 126 can include a cap, valve or similar structure configured to allow air or a gas to enter the drainage lumen 122 but to prevent air, gas, or fluid from escaping from the drainage lumen 122. In an embodiment, the sample port 124 and the inlet vent 126 can be separate structures. In an embodiment, the sample port 124 and the inlet vent 126 can be the same structure. In an embodiment, the drainage tube 120 can include one or more of the sample port 124 or inlet vents 126. As shown in FIG. 1, the sample port 124 and the inlet vent 126 can be disposed proximate a distal end of the drainage tube 120 and can be disposed distally of the distal pump 200. However, it will be appreciated that one or more of the sample port(s) 124 or the inlet vent(s) 126 can be disposed at other positions along the length of the drainage tube, for example between the distal pump 200 and the proximal pump 300, or proximal of the proximal pump 300.

FIGS. 2A-3C show further details of the one or more vacuum pumps disposed in-line with the drainage tube 120.

Figure 2A:
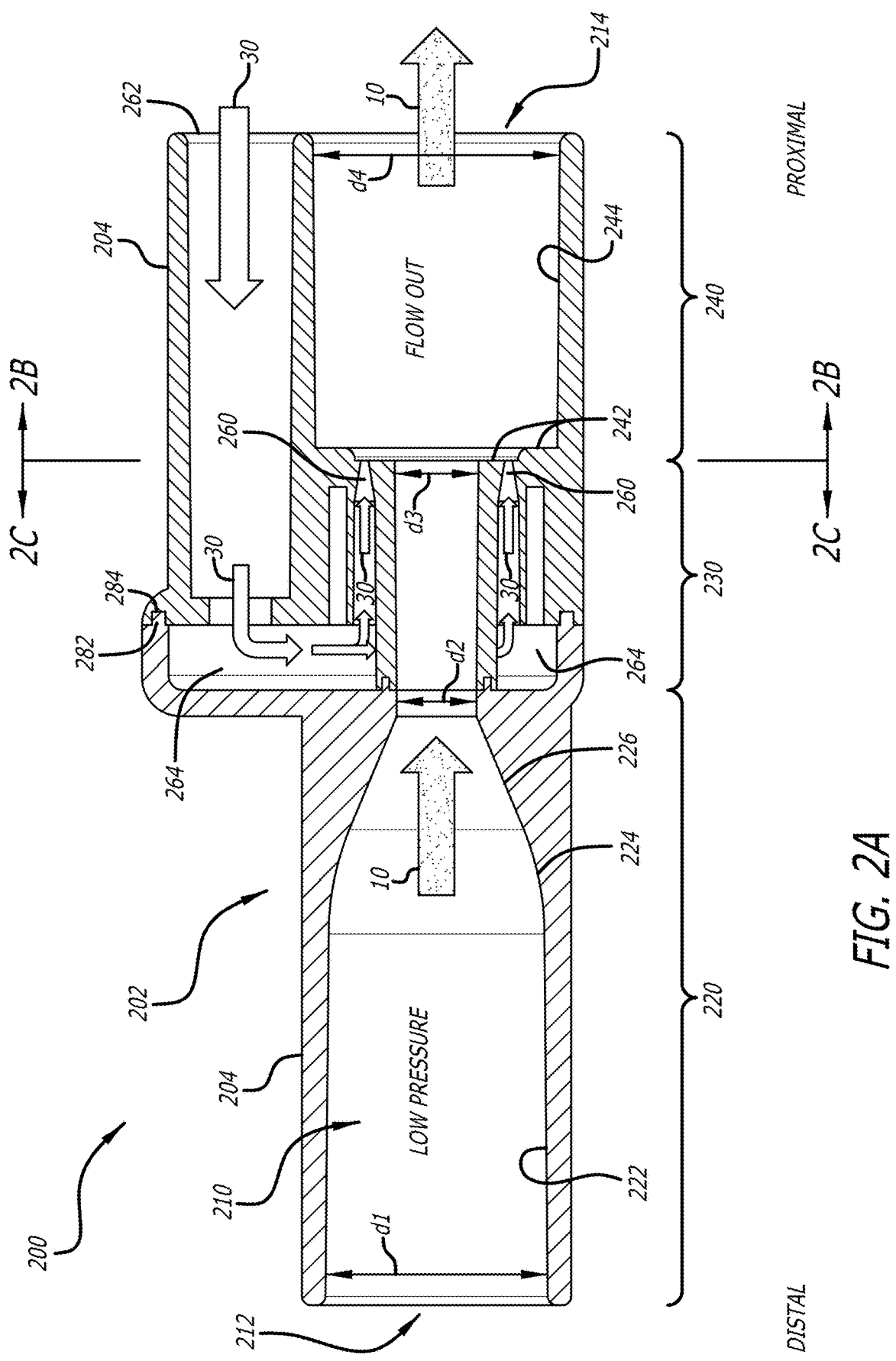
FIG. 2A illustrates a cross-sectional side view of a distal pump of the fluid drainage system of FIG. 1, in accordance with embodiments disclosed herein.
Figure 2C:
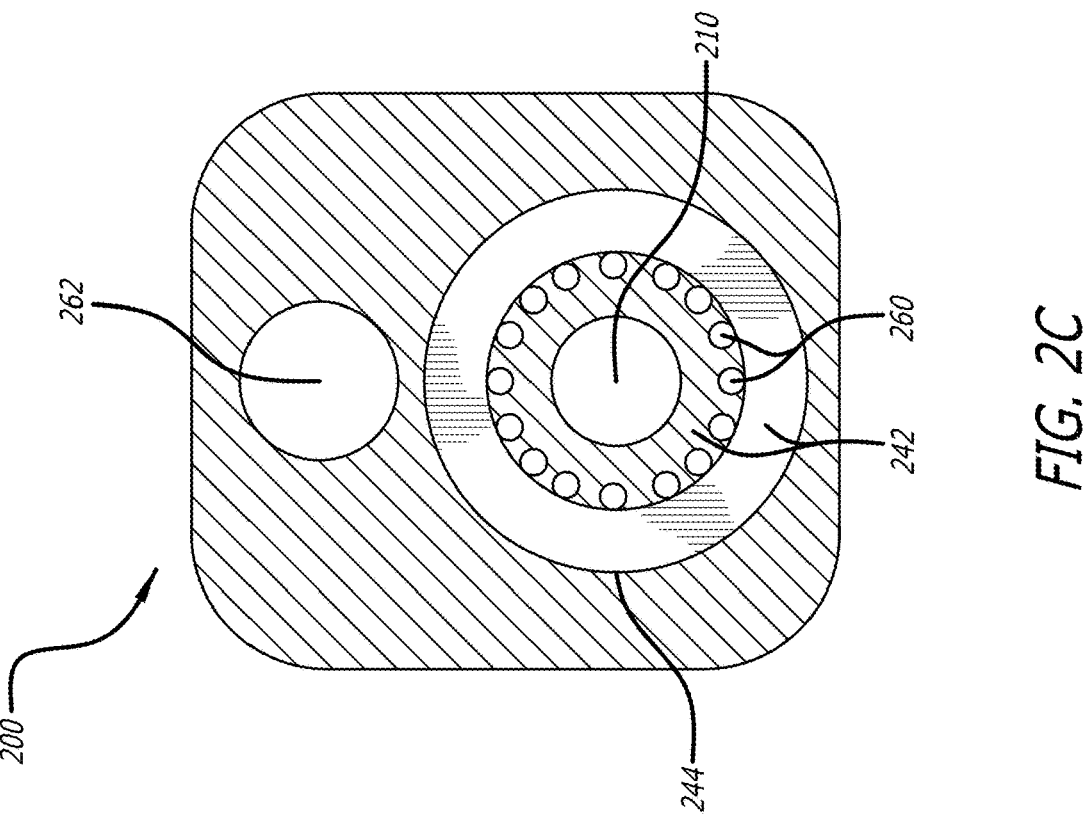
FIGS. 2B-2C illustrates a cross-sectional axial view of embodiments of a drive nozzle, in accordance with embodiments disclosed herein.
Figure 2B:
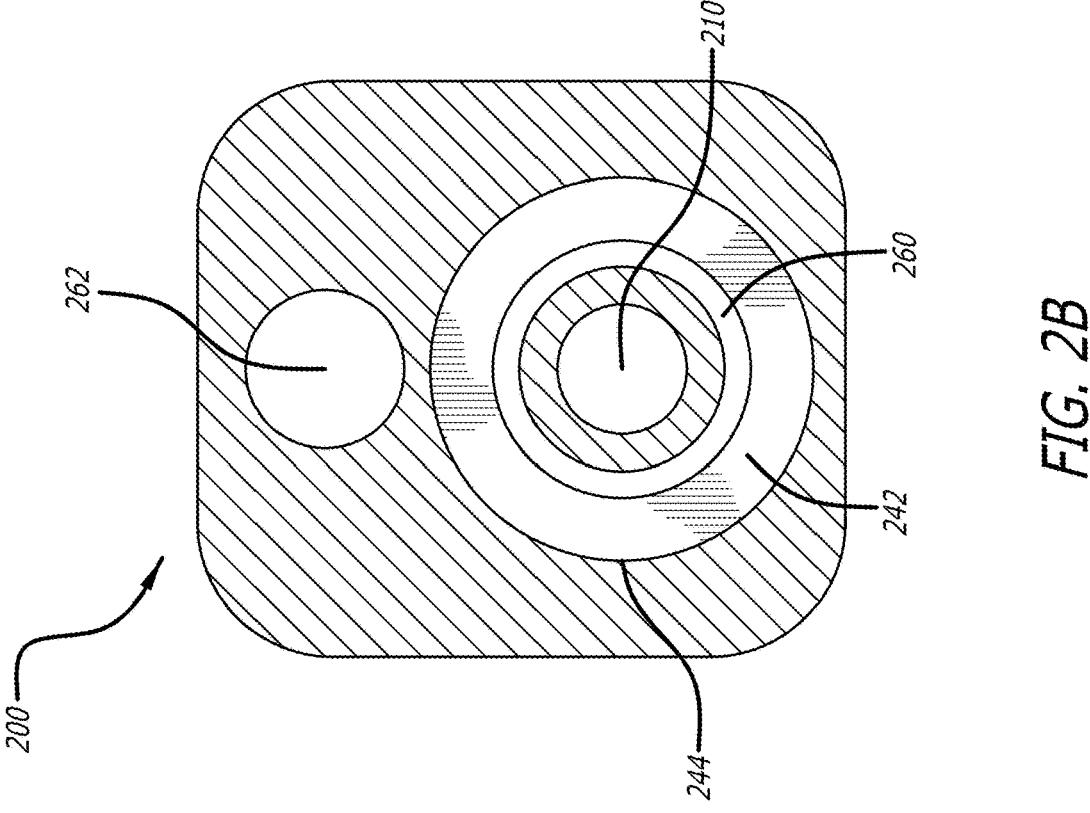

FIGS. 2A-2C show details of a first vacuum pump 200 disposed proximate a distal end of the drainage tube 120. The distal pump 200 can be an ejector pump that feeds a pressurized drive fluid 30 into a drainage lumen 210 to entrain a fluid, e.g. a drainage fluid 10, disposed within the drainage lumen 210. As used herein, the drainage fluid 10 can be a gas, liquid, or a mixed combination thereof, such as a vapor, or droplets of liquid mixed with gas. The distal pump 200 can include a housing 202 formed of a first housing piece 204 and a second housing piece 206. In an embodiment, the first housing piece 204 is disposed distally of the second housing piece 206. A distal surface of the first housing piece 204 can engage a proximal surface the second housing piece 206 to form the housing 202. The first housing piece 204 can be attached to the second housing piece 206 using adhesive, bonding, welding, or the like. Further, one of the first housing piece 204 or the second housing piece 206 can include a protrusion 282, configured to engage a recess 284 disposed on the opposing piece to align and secure the first housing piece 204 with the second housing piece 206. However, it will be appreciated that various numbers or configurations of protrusions 282 and recesses 284 are contemplated. Further, it will be appreciated that various attachment mechanisms including lugs, clips, snap-fit, interference fit, press fit engagements, or combinations thereof, are also contemplated to fall within the scope of the present invention. In an embodiment, the housing 202 can be formed as a single unitary piece by injection molding, 3D printing, or similar suitable means.

The distal vacuum pump 200 can include a drainage lumen 210 extending along a longitudinal axis from a drainage inlet 212 disposed at a distal end to a drainage outlet 214 disposed at a proximal end. The drainage lumen 210 can define a substantially circular cross-sectional shape. However, it will be appreciated that other cross-sectional shapes are also contemplated including square, triangular, hexagonal or any closed curve, regular or irregular polygonal shapes. In an embodiment, the cross-sectional shape can define a radially symmetrical shape.

In an embodiment the inlet 212 can be releasably coupled with a distal portion of the drainage tube 120. In an embodiment the inlet 212 can be integrally formed with a distal portion of the drainage tube 120. In an embodiment the drainage outlet 214 can be releasably coupled with a proximal portion of the drainage tube 120. In an embodiment the outlet 214 can be integrally formed with a distal portion of the drainage tube 120. As such, the drainage lumen 210 of the distal vacuum pump 200 can be disposed in-line a lumen 122 of the drainage tube 120.

The drainage lumen 210 of the distal vacuum pump 200 can include a converging section 220, a diffuser section 230, and a diverging section 240. The converging section 220 can extend from the drainage inlet 212 to a distal end of the diffuser section 230. The diffuser section 230 can extend from a proximal end of the converging section 220 to a distal end of the diverging section 240. The diverging section 240 can extend from a proximal end of the diffuser section 230 to a drainage outlet 214.

The drainage lumen 210 of the converging section 220 can define a first diameter (d1) proximate the drainage inlet 212 and a second diameter (d2), less than the first diameter (d1) proximate the diffuser section 230. In an embodiment, the drainage lumen 210 of the converging section 220 can define a continuous change in diameter between the first diameter (d1) and second diameter (d2), i.e. defining a continuous, tapered, cone shape.

In an embodiment, the drainage lumen 210 of the converging section 220 can define a discontinuous change in diameter between the first diameter (d1) and second diameter (d2). For example, as shown in FIG. 2A, the converging section 220 can include an accumulation portion 222 that defines a gradual reduction in diameter from the first diameter (d1), such that a wall of the accumulation portion 222 extends at a shallow angle of between 1° and 5°, relative to the longitudinal axis. However, greater or lesser angles are also contemplated. In an embodiment, a wall of the accumulation portion 222 can extend parallel to a longitudinal axis.

The converging section 220 can also include a shoulder portion 224 wherein an angle of the wall of the drainage lumen 210 can vary between 5° and 20°, relative to the longitudinal axis. However, greater or lesser angles are also contemplated. The converging section 220 can also include an acceleration portion 226 that defines a greater reduction in diameter over a given longitudinal distance, than the accumulation portion 222, such that a wall of the drainage lumen 210 extends at an angle of between 20° and 40°, relative to the longitudinal axis. However, greater or lesser angles are also contemplated. It will be appreciated that embodiments of the converging section 220 can include various numbers, orders, and configurations of one of the accumulation portion 222, shoulder portion 224, or the acceleration portion 226.

In an embodiment, the drainage lumen 210 of the diffuser section 230 can define a substantially continuous diameter such that a diameter of the drainage lumen 210 at a distal end of the diffuser section 230, e.g. second diameter (d2) is substantially the same as a diameter of the drainage lumen 210 at a proximal end of the diffuser section 230, e.g. third diameter (d3). Worded differently, a wall of the drainage lumen 210 of the diffuser section 230 can extend substantially parallel to the longitudinal axis.

In an embodiment, the drainage lumen 210 of the diffuser section 230 can define a diverging diameter shape such that a diameter of the drainage lumen 210 at a distal end of the diffuser section 230, e.g. second diameter (d2) is less than a diameter of the drainage lumen 210 at a proximal end of the diffuser section 230, e.g. third diameter (d3). Worded differently, a wall of the drainage lumen 210 of the diffuser section 230 can extend at an angle relative to the longitudinal axis.

In an embodiment, the drainage lumen 210 of the diffuser section 230 can define a converging diameter shape such that a diameter of the drainage lumen 210 at a distal end of the diffuser section 230, e.g. second diameter (d2) is greater than a diameter of the drainage lumen 210 at a proximal end of the diffuser section 230, e.g. third diameter (d3). In an embodiment, the diffuser section 230 can define a continuous change in diameter between the second diameter (d2) and the third diameter (d3). In an embodiment, the diffuser section 230 can define a discontinuous change in diameter between the second diameter (d2) and the third diameter (d3).

The drainage lumen 210 of the diverging section 240 can define a diverging diameter shape diverging from the third diameter (d3) disposed proximate the distal end of the diverging section 240, to a fourth diameter (d4) disposed proximate the drainage outlet 214, the fourth diameter (d4) being greater than the third diameter (d3).

In an embodiment, the drainage lumen 210 of the diverging section 240 can define a continuous change in diameter between the third diameter (d3) and the fourth diameter (d4), e.g. to define an inverse tapering, cone shape relative to the direction of flow through the drainage lumen 210. In an embodiment, the drainage lumen 210 of the diverging section 240 can define a discontinuous change in diameter between the third diameter (d3) and the fourth diameter (d4). For example, the diverging section 240 can include a stepped expansion 242 in diameter of the drainage lumen 210 wherein a portion of the wall of the drainage lumen 210 extends perpendicular to the longitudinal axis. Further, the diverging section 240 can include an expansion portion 244 wherein a portion of the wall of the drainage lumen 210 can extend at a shallow angle of between 1° and 5°, relative to the longitudinal axis. However, greater or lesser angles are also contemplated. In an embodiment, a wall of the expansion portion 244 can extend parallel to the longitudinal axis. It will be appreciated that embodiments of the diverging section 240 can include various numbers, orders, and configurations of stepped portions 242 or expansion portion 244. In an embodiment one or more transition edges between the converging section 320, diffuser section 330, diverging section 340, or portions thereof, can include a chamfered edge.

The distal vacuum pump 200 can further include a drive nozzle 260. In an embodiment, as shown in FIG. 2B, the drive nozzle 260 can define a ring-shaped cross-section extending annularly about the diffuser section 230, when viewed in cross-section to the longitudinal axis. In an embodiment, as shown in FIG. 2C, the drive nozzle 260 can include an array of nozzles arranged in a ring shape extending annularly about the diffuser section 230, when viewed in cross-section to the longitudinal axis.

The distal vacuum pump 200 can include a drive fluid inlet 262 that can provide a pressurized drive fluid 30 to a plenum 264. The plenum 264 can provide the pressurized drive fluid 30 to the drive nozzle 260. In an embodiment, the drive fluid 30 can include pressurized air, however, any suitable pressurized gas or liquid are also contemplated. In an embodiment, the drive fluid 30 can be provided by a separate line. In an embodiment, the drainage tube 120 can include a dual lumen, a first lumen can define the drainage lumen 122, a second lumen can provide a pressurized drive fluid 30 to one or more vacuum pumps, e.g. the distal pump 200 or proximal pump 300.

In an exemplary method of use, a drive fluid 30 is provided to the drive fluid inlet 262 and supplied through the plenum 264 to the drive nozzle 260. The drive nozzle 260 is designed to provide a drive jet into the divergent section 240 that entrains a drainage fluid 10, e.g. a gas, liquid, or mixed combination thereof, disposed within the drainage lumen 210. More specifically, the jet of drive fluid 30 is provided at a stepped portion 242 of the divergent section 240 that substantially aligns with a transition between the diffuser section 230 and the divergent section 240. The drive fluid 30 entrains a drainage fluid 10 disposed in the diffuser section 230 that creates a low pressure in the convergent section 220, which draws a drainage fluid 10 from the drainage inlet 212 proximally into the drainage lumen 210. Further, the drive jet 30 urges the drainage fluid 10 through the divergent section 240, through the drainage outlet 214 proximally into a proximal portion of the drainage tube 120.

Advantageously, the configuration of the drainage lumen 210 together with the drive jet 30 induces an amplifying effect, whereby a force of the pressurized drive fluid 30 is less than a suction force applied to the drainage fluid 10 at the drainage inlet 212. Advantageously, the distal vacuum pump 200 can draw either a columned drainage fluid 10 or a mixed drainage fluid 10 (e.g. liquid and gas mixture) from a distal portion of the drainage tube 120, disposed distally of the vacuum pump 200, through the drainage lumen 210, and urge the drainage fluid 10 proximally through the drainage tube 120.

Figure 3A:
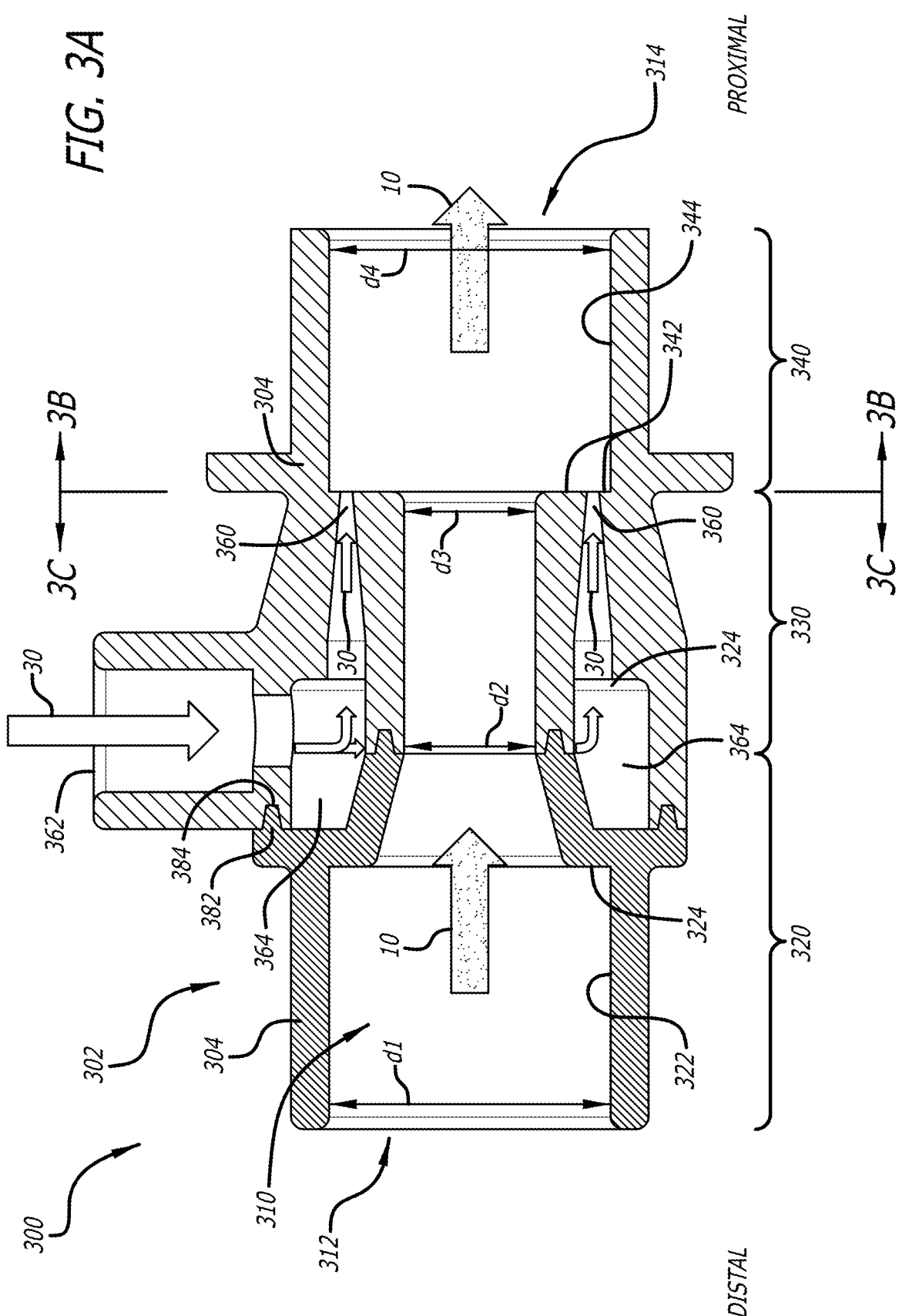
FIG. 3A illustrates a cross-sectional side view of a proximal pump of the fluid drainage system of FIG. 1, in accordance with embodiments disclosed herein.
Figure 3C:
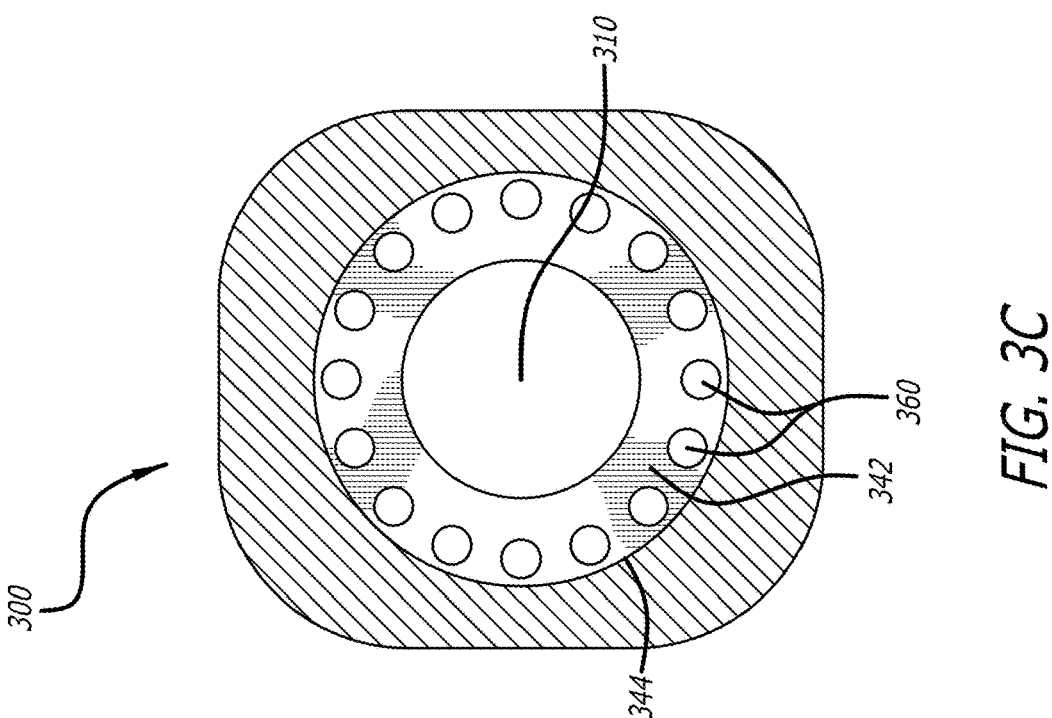
FIGS. 3B-3C illustrates a cross-sectional axial view of embodiments of a drive nozzle, in accordance with embodiments disclosed herein.
Figure 3B:
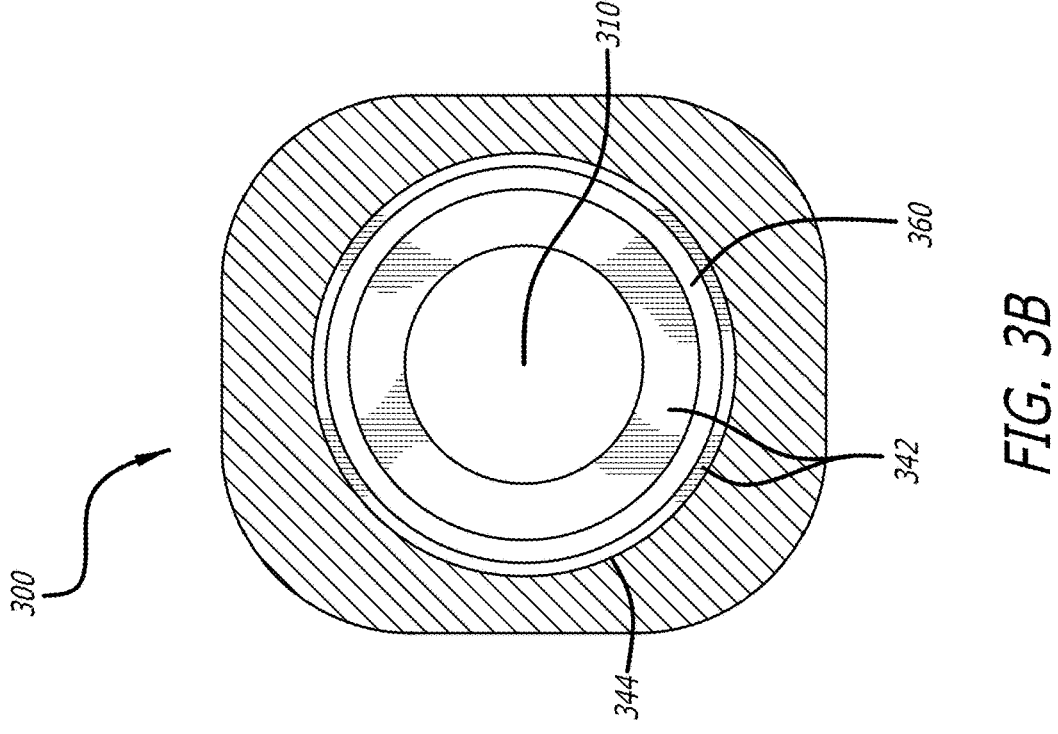

FIGS. 3A-3B show further details of the proximal vacuum pump 300. The proximal pump 300 can include a housing 302 formed of a first housing piece 304 and a second housing piece 306. In an embodiment, the first housing piece 304 is disposed distally of the second housing piece 306. A distal surface of the first housing piece 304 can engage a proximal surface the second housing piece 306 to form the housing 302.

The first housing piece 304 can be attached to the second housing piece 306 using adhesive, bonding, welding, or the like. Further, one of the first housing piece 304 or the second housing piece 306 can include a protrusion 382, configured to engage a recess 384 disposed on the opposing piece to align and secure the first housing piece 304 with the second housing piece 306. However, it will be appreciated that various numbers or configurations of protrusions 382 and recesses 384 are contemplated. Further, it will be appreciated that various attachment mechanisms including lugs, clips, snap-fit, interference fit, press fit engagements, or combinations thereof, are also contemplated to fall within the scope of the present invention. In an embodiment, the housing 302 can be formed as a single unitary piece by injection molding, 3D printing, or similar suitable means.

The proximal vacuum pump 300 can generally include a drainage lumen 310 extending along a longitudinal axis from a drainage inlet 312 disposed at a distal end to a drainage outlet 314 disposed at the proximal end. The drainage lumen 310 can define a substantially circular cross-sectional shape. However, it will be appreciated that other cross-sectional shapes are also contemplated including square, triangular, hexagonal or any closed curve, regular or irregular polygonal shapes. In an embodiment, the cross-sectional shape can define a radially symmetrical shape.

In an embodiment the inlet 312 can be releasably coupled with a distal portion of the drainage tube 120. In an embodiment the inlet 312 can be integrally formed with a distal portion of the drainage tube 120. In an embodiment the outlet 314 can be releasably coupled with a proximal portion of the drainage tube 120. In an embodiment the outlet 314 can be integrally formed with a distal portion of the drainage tube 120. As such, the drainage lumen 310 of the proximal vacuum pump 300 can be disposed in-line with a lumen 122 of the drainage tube 120.

The proximal vacuum pump 300 can include a converging section 320, a diffuser section 330, and a diverging section 340. The converging section 320 can extend from the drainage inlet 312 to a distal end of the diffuser section 330. The diffuser section 330 can extend from a proximal end of the converging section 320 to a distal end of the diverging section 340. The diverging section 340 can extend from a proximal end of the diffuser section 330 to a drainage outlet 314.

The drainage lumen 310 of the converging section 320 can define a first diameter (d1) proximate the drainage inlet 312 and a second diameter (d2), less than the first diameter (d1) proximate the diffuser section 330. In an embodiment, the drainage lumen 310 of the converging section 320 can define a continuous change in diameter between the first diameter (d1) and second diameter (d2) i.e. defining a continuous, tapered, cone shape.

In an embodiment, the drainage lumen 310 of the converging section 320 can define a discontinuous change in diameter between the first diameter (d1) and second diameter (d2). For example, as shown in FIG. 3A, the converging section 320 can include an accumulation portion 322 wherein a wall of the accumulation portion 322 extends substantially parallel to a longitudinal axis. In an embodiment, the accumulation portion 322 can define a gradual reduction in diameter from the first diameter (d1), such that a wall of the accumulation portion 322 extends at an angle of between 1° and 5°, relative to the longitudinal axis. However, greater or lesser angles are also contemplated.

The converging section 320 can also include a stepped portion 324 wherein an angle of the wall of the converging section 320 extends perpendicular relative to the longitudinal axis. The converging section 320 can also include an acceleration portion 326 that defines a greater reduction in diameter over a given longitudinal distance, than the accumulation portion 322, such that a wall of the acceleration portion 326 extends at an angle of between 10° and 40°, relative to the longitudinal axis. However, greater or lesser angles are also contemplated. It will be appreciated that embodiments of the converging section 320 can include various numbers, orders, and configurations of one of the accumulation portion 322, shoulder portion 324, or the acceleration portion 326.

In an embodiment, the drainage lumen 310 of the diffuser section 330 can define a substantially continuous diameter such that a diameter of the drainage lumen 310 at a distal end of the diffuser section 330, e.g. second diameter (d2) is substantially the same as a diameter of the drainage lumen 310 at a proximal end of the diffuser section 330, e.g. third diameter (d3). Worded differently, a wall of the drainage lumen 310 of the diffuser section 330 can extend substantially parallel to the longitudinal axis.

In an embodiment, the drainage lumen 310 of the diffuser section 330 can define a diverging diameter shape such that a diameter of the drainage lumen 310 at a distal end of the diffuser section 330, e.g. second diameter (d2) is less than a diameter of the drainage lumen 310 at a proximal end of the diffuser section 330, e.g. third diameter (d3). Worded differently, a wall of the drainage lumen 310 of the diffuser section 330 can extend at an angle relative to the longitudinal axis.

In an embodiment, the drainage lumen 310 of the diffuser section 330 can define a converging diameter shape such that a diameter of the drainage lumen 310 at a distal end of the diffuser section 330, e.g. second diameter (d2) is greater than a diameter of the drainage lumen 310 at a proximal end of the diffuser section 330, e.g. third diameter (d3). In an embodiment, the diffuser section 330 can define a continuous change in diameter between the second diameter (d2) and the third diameter (d3). In an embodiment, the diffuser section 330 can define a discontinuous change in diameter between the second diameter (d2) and the third diameter (d3).

The drainage lumen 310 of the diverging section 340 can define a diverging diameter shape diverging from the third diameter (d3) disposed proximate the distal end of the diverging section 340, to a fourth diameter (d4) disposed proximate the drainage outlet 314, the fourth diameter (d4) being greater than the third diameter (d3).

In an embodiment, the drainage lumen 310 of the diverging section 340 can define a continuous change in diameter between the third diameter (d3) and the fourth diameter (d4) e.g. to define an inverse tapering, cone shape relative to the direction of flow through the drainage lumen 310. In an embodiment, the drainage lumen 310 of the diverging section 340 can define a discontinuous change in diameter between the third diameter (d3) and the fourth diameter (d4). For example, the diverging section 340 can include a stepped expansion 342 in diameter of the drainage lumen 310 wherein a portion of the wall of the drainage lumen 310 extends perpendicular to the longitudinal axis. Further, the diverging section 340 can include an expansion portion 344 wherein a portion of the wall of the drainage lumen 310 can extend at an angle of between 1° and 5°, relative to the longitudinal axis. However, greater or lesser angles are also contemplated. In an embodiment, a wall of the expansion portion 344 can extend substantially parallel to a longitudinal axis.

It will be appreciated that embodiments of the diverging section 340 can include various numbers, orders, and configurations of stepped portions 342 or expansion portion 344. In an embodiment, one or more transition edges between the converging section 320, diffuser section 330, diverging section 340, or portions thereof, can include a chamfered edge.

The proximal vacuum pump 300 can further include a drive nozzle 360. In an embodiment, as shown in FIG. 3B, the drive nozzle 360 can define a ring shape extending annularly about the diffuser section 330, when viewed in cross-section to the longitudinal axis. In an embodiment, as shown in FIG. 3C, the drive nozzle 360 can include an array of nozzles arranged in a ring shape extending annularly about the diffuser section 330, when viewed in cross-section to the longitudinal axis.

The proximal vacuum pump 300 can include a drive fluid inlet 362 that can provide a pressurized drive fluid 30 to a plenum 364. The plenum 364 can provide the pressurized drive fluid 30 to the drive nozzle 360. In an embodiment, the drive fluid 30 can include pressurized air, however, any suitable pressurized gas or liquid are also contemplated.

In an embodiment, the distal pump 200 and the proximal pump 300 can be identical. In an embodiment, the distal pump 200 and the proximal pump 300 can be different, in either configuration and/or properties of the pump. For example, the pumps can differ in overall size, configuration of the drainage lumen profile, configuration of the drive nozzle/nozzle array, number of drive nozzles, drive fluid inlet resistance, combinations thereof, or the like.

In an embodiment, one of the distal or proximal pumps 200, 300, can be tuned differently from the other, such as providing a different vacuum force or providing greater or lesser volume movement, or the like. For example, a larger overall pump can provide a greater movement of volume of fluid. By contrast, an overall smaller pump, including identical proportions to the larger pump, can achieve a harder vacuum (lower absolute pressure). Further, individual pump characteristics can be further modified by modifying a volume or pressure of drive fluid 30 supplied thereto. As such each of the proximal pump 200 and the distal pump 300 can be tuned to provide specific pump characteristics for their respective location along the drainage tube 120.

In an exemplary method of use, a drive fluid 30 is provided to the drive fluid inlet 362 and supplied through the plenum 364 to the drive nozzle 360. The drive nozzle 360 provides a drive jet into the divergent section 340 that entrains a drainage fluid 10, e.g. a gas, liquid, or mixed combination thereof, disposed in the drainage lumen 310. More specifically, the jet of drive fluid 30 is provided at a stepped portion 342 of the divergent section 240 that substantially aligns with a transition between the diffuser section 330 and the divergent section 240. The drive fluid 30 entrains a drainage fluid 10 disposed in the diffuser section 330 that creates a low pressure in the convergent section 320, which draws a drainage fluid 10 from the drainage inlet 312, proximally through the drainage lumen 310. Further, the drive jet urges the drainage fluid 10 through the divergent section 340, proximally into a proximal portion of the drainage tube 120.

Advantageously, the configuration of the drainage lumen 310 together with the drive jet 30 induces an amplifying effect, whereby a force of the pressurized drive fluid 30 is less than a suction force applied to the drainage fluid 10 at the drainage inlet 312. Advantageously, the proximal vacuum pump 300 can draw either a columned drainage fluid 10 or a mixed drainage fluid 10 (e.g. liquid and gas mixture) from a portion of the drainage tube 120, disposed distally of the proximal vacuum pump 300, through the drainage lumen 310, and urge the drainage fluid 10 proximally through the drainage tube 120 and into the collection container.

Advantageously, the assisted fluid drainage system 100 including the ejector pumps 200, 300, can prevent the formation of dependent loops within the drainage lumen 122.

Advantageously, the system 100 can operate under lower pressure conditions and does not require a valve to separate fluid communication between the catheter 110 and the drainage tube 120 during operation. The catheter 110, including columnized fluid disposed within the catheter lumen 112, can provide a greater flow resistance than a flow resistance of the inlet vent 126. As such the distal pump 200 creates a vacuum that entrains a fluid, which includes liquid disposed within the drainage lumen 122 and air from the inlet vent 126. The vacuum is not communicated through catheter 110 to the patient. Instead fluid from the catheter 110 can transfer (e.g. by gravity, diffusion, etc.) to the drainage lumen 122 before being entrained by the distal pump 200. Since the distal pump 200 operating at the lower pressure is unable to urge the fluid through the proximal portion of the drainage lumen 122, subsequent pumps disposed along the drainage lumen, e.g. proximal pump 300, can continue to urge the fluid through the drainage tube 120 to the collection container 130.

In an embodiment, the vacuum pumps 200, 300 can work in conjunction to urge a drainage fluid 10 through the drainage tube 120. The influence of a pump on a fluid within a pipe can be limited by a number of factors, e.g. fluid temperature, state, gas or fluid mix, incline, etc. As such the influence of a pump can be limited to a given longitudinal length. To overcome these limitations, a greater vacuum force can be applied by the pump to move a fluid from the catheter 110, through the drainage tube 120, and into the collection container 130. However, such a force can cause trauma to a patient, as such a catheter 110 must be disconnected from the drainage tube 120, e.g. by shutting a valve or the like, before the pump can clear the drainage line.

Embodiments disclosed herein teach one or more pumps 200, 300 disposed along the drainage tube 120. The pumps 200, 300 can operate at lower forces to allow the pumps to operate while the drainage tube 120 remains in fluid communication with the catheter 110. While the pumps 200, 300 operating at lower forces, have a shorter length of influence along the drainage lumen, the pumps 200, 300 can work in conjunction to influence the entire length of the drainage tube 120. For example, as shown in FIG. 4A a larger pump 400 providing a greater force of drive fluid 30A can have a greater influence on the drainage fluid 10, i.e. influencing the drainage fluid 10 over a greater longitudinal distance of tube 120, distance (x). This distance can be distal (upstream) of the pump and require greater suction or proximal (downstream) and require greater pushing.

As shown in FIG. 4B, where a lesser force of driver fluid 30B is applied, the pump has a lesser influence on the drainage fluid 10, i.e. influencing drainage fluid 10 over a shorter longitudinal distance of tube 120, distance (y). However, two or more pumps, e.g. pumps 200, 300, can operate at the lesser driver fluid force 30A and work in conjunction to influence the same distance (where x=2y) of drainage tube 120.

Further still a difference between a columnized drainage fluid 10A i.e. a drainage fluid 10 that fills the drainage lumen, and a mixed drainage fluid 10B, i.e. a mix gas and liquid can further affect the influence length of a pump. For example, FIG. 4A shows a columnized drainage fluid 10A along a distance (x). Should this be a mixed drainage fluid (e.g. FIG. 4B) a still greater force drive fluid 30 would be required to influence the same distance (x).

As noted, high pump forces can have a detrimental effect on a patient should the catheter 110 remain in fluid communication with the drainage tube when a sufficient driver fluid force 30 is applied to a single pump 400 to urge the drainage fluid 10 along an entire length of the drainage tube 120. As such, the catheter 110 must be fluidly disconnected, e.g. by shutting a valve, before such a pump can operate. By contrast, embodiments disclosed herein disclose two or more pumps operating at a lower driver fluid pressure 30 to urge a drainage fluid through a portion of the drainage lumen 122. An adjacent pump can then be configured to urge the drainage fluid 10 through an adjacent portion of drainage lumen 122.

Advantageously, embodiments described herein can operate to urge a drainage fluid 10 through the drainage lumen 122 while the catheter 110 remains in fluid communication with the drainage tube 120. This allows the pumps 200, 300 to operate continuously while the catheter 110 is in place, without requiring coordinated closing and opening of valves or starting/stopping a pumps. As such, the system 100 requires a simplified operation and manufacture, reducing associated costs.

As noted, a number of variables can affect the influence distance of a pump. In an embodiment, the pumps 200, 300 can be tuned such that adjacent influence distances (y) overlap under mixed drainage fluid 10B conditions. If parameters of the drainage fluid change such that adjacent influence distances (y) do not overlap then drainage fluid 10 can potentially pool between pumps 200, 300. However, pooled fluid 10 provides a columnized fluid 10 that can cause the influence distance (y) to increase. As such the system 100 and pumps 200, 300 can be tuned to self-regulate.

In an embodiment, the one or more vacuum pumps 200, 300 can operate intermittently. In an embodiment, the system 100 can include a controller 150 configured to control operation of one or more vacuum pumps 200, 300. The controller include logic configured to operate one or more vacuum pumps 200, 300 continuously, intermittently, concurrently, sequentially, alternately, or combinations thereof. The controller 150 operate the pumps 200, 300 concurrently to move the drainage fluid 10 through the drainage tube 120. In an embodiment, the one or more pumps 200, 300 can be operated sequentially or alternately, to move a fluid 10 through the drainage tube 120 in a "wave-like" manner.

In an embodiment, the controller 150 can operate the pumps 200, 300 in response to a trigger. For example, the controller 150 can trigger operation of the one or more pumps 200, 300 in response to a given time interval elapsing, in response to an input such as the presence of liquid or an increase in fluid pressure within the drainage lumen, or combinations thereof. In an embodiment, the controller 150 can be communicatively coupled with a network 160, or similar external computing device such as an electronic health records system, intranet, mobile device, centralized or decentralized network or the like. This can allow a user to operate the controller 150 remotely, or receive information about the system 100.

Advantageously, the configuration of the pumps 200, 300 does not inhibit fluid flow through drainage tubes 120 even when the pumps are not operating. This allows the drainage system 100 to function as a gravity driven system when the pumps are not operating increasing power efficiency of the system 100. In an embodiment, atmospheric gas (air) 20 can be provided to the system 100 by way of the inlet vent 124. This atmospheric gas 20 can be mixed with the drainage fluid 10 and drawn through the drainage tube 120 into the container 130. The fluid 10 can then be collected in the container 130 and excess gas can be vented from the system 100 by way of outlet vent 134. Advantageously, the one or more ejector pumps 200, 300 require no moving parts which can minimize maintenance costs and simplify manufacturing, along with associated cost savings. Further, the one or more pumps 200, 300 can operate highly efficiently where a given force (f) of pressurized drive fluid produces a greater force (>f) of vacuum pressure.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A method of draining a bodily fluid, comprising:
coupling a drainage tube between a proximal ejector pump and a distal ejector pump, wherein:
   at least one of the proximal ejector pump and the distal ejector pump includes a converging section, a diffuser section, and a diverging section,
   a diameter of the diffuser section is less than a diameter of the converging section or the diverging section, and
   the diverging section includes a stepped expansion portion;
providing a drive fluid to the stepped expansion portion via a drive nozzle; and
moving the bodily fluid through a lumen of the drainage tube via at least one of the proximal ejector pump and the distal ejector pump.

2. The method according to claim 1, further comprising coupling a collection container to the proximal ejector pump to receive the bodily fluid from the lumen of the drainage tube.

3. The method according to claim 2, wherein the bodily fluid is urine, and wherein the distal ejector pump is in fluid communication with a urinary catheter.

4. The method according to claim 3, further comprising permitting gas to enter the lumen of the drainage tube via an inlet vent disposed distal of the distal ejector pump and proximal of the urinary catheter.

5. The method according to claim 4, wherein the collection container includes an outlet vent, wherein the outlet vent further comprises permitting gas to exit via the outlet vent.

6. The method according to claim 1, wherein moving the bodily fluid through the lumen of the drainage tube comprises operating both the proximal ejector pump and the distal ejector pump intermittently.

7. The method according to claim 6, wherein moving the bodily fluid through the lumen of the drainage tube comprises operating the proximal ejector pump and the distal ejector pump sequentially.

8. The method according to claim 1, wherein the drive nozzle comprises a ring drive nozzle positioned annularly about the lumen of the drainage tube.

9. The method according to claim 1, wherein the at least one of the proximal ejector pump and the distal ejector pump includes an array of drive nozzles arranged in a ring-shaped formation extending annularly about the lumen of the drainage tube.

10. The method according to claim 1, further comprising creating a vacuum in the at least one of the proximal ejector pump and the distal ejector pump, the vacuum influencing a portion of the lumen of the drainage tube less than an entire length of the drainage tube.

11. The method according to claim 1, wherein the proximal ejector pump includes the converging section, the diffuser section, and the diverging section, wherein the distal ejector pump includes a distal converging section, a distal diffuser section, and a distal diverging section, wherein a diameter of the distal diffuser section is less than a diameter of the distal converging section or the distal diverging section, and wherein the distal diverging section includes a distal stepped expansion portion.

12. The method according to claim 1, wherein a controller is coupled to the proximal ejector pump and the distal ejector pump, further comprising initiating operation of one or both of the proximal ejector pump and the distal ejector pump in response to an event.

13. The method according to claim 12, wherein the event is selected from the group consisting of an elapsed time period, presence of the bodily fluid, an increase in fluid pressure in the lumen of the drainage tube, and combinations thereof.

14. The method according to claim 12, wherein the controller is communicatively coupled to a network, further comprising transmitting information from the controller to the network.

15. The method according to claim 14, wherein the network comprises an electronic health records system.

* * * * *